United States Patent [19]
Durant et al.

[11] Patent Number: 6,013,675
[45] Date of Patent: Jan. 11, 2000

[54] THERAPEUTIC SUBSTITUTED GUANIDINES

[75] Inventors: Graham J. Durant, Cambridge; Lain-Yen Hu, Bedford; Sharad Magar, Somerville, all of Mass.

[73] Assignee: Cambridge NeuroScience, Inc., Cambridge, Mass.

[21] Appl. No.: 08/459,974

[22] Filed: Jun. 2, 1995

Related U.S. Application Data

[63] Continuation of application No. PCT/US94/13245, Nov. 22, 1994, abandoned, and a continuation-in-part of application No. 08/156,773, Nov. 23, 1993, abandoned.

[51] Int. Cl.$^7$ ...................... A61K 31/155; C07C 279/18
[52] U.S. Cl. .................. 514/634; 514/524; 514/633; 558/413; 564/229; 564/230; 564/237; 564/238; 564/239
[58] Field of Search .................. 514/633, 634, 514/524; 564/229, 238, 239, 230, 237; 558/413

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser et al. | 564/238 |
| 1,642,180 | 9/1927 | Scott | 564/238 |
| 1,672,431 | 6/1928 | Schotte | 564/238 |
| 1,677,235 | 7/1928 | Heuser | 564/238 |
| 1,730,388 | 10/1929 | Brooks | 564/238 |
| 1,756,315 | 4/1930 | terHorst | 564/238 |
| 1,795,398 | 3/1931 | Schotte | 564/238 |
| 1,850,682 | 3/1932 | Meiss | 564/238 |
| 1,915,922 | 6/1933 | Christmann et al. | 564/238 |
| 2,145,214 | 1/1939 | Jayne, Jr. | 167/37 |
| 2,254,009 | 8/1941 | Hechenbleikner | 260/564 |
| 2,274,476 | 2/1942 | Hechenbleikner | 167/30 |
| 2,289,541 | 7/1942 | Ericks et al. | 167/22 |
| 2,362,915 | 11/1944 | MacGregor | 3/74 |
| 2,422,889 | 6/1947 | Curd et al. | 260/251 |
| 2,633,474 | 3/1953 | Beaver | 260/565 |
| 2,704,710 | 3/1955 | Sprung | 95/2 |
| 3,117,994 | 1/1964 | McKay et al. | 260/565 |
| 3,140,231 | 7/1964 | Luskin et al. | 167/65 |
| 3,159,676 | 12/1964 | Spickett et al. | 360/564 |
| 3,168,562 | 2/1965 | Walton et al. | 564/237 |
| 3,228,975 | 1/1966 | Abraham et al. | 260/501 |
| 3,248,426 | 4/1966 | Dvornik | 260/564 |
| 3,252,861 | 5/1966 | Mull | 167/65 |
| 3,270,054 | 8/1966 | Gagneux et al. | 260/564 |
| 3,283,003 | 11/1966 | Jack et al. | 260/564 |
| 3,301,755 | 1/1967 | Mull | 167/65 |
| 3,320,229 | 5/1967 | Szabo et al. | 260/96.5 |
| 3,391,189 | 7/1968 | Mull | 260/564 |
| 3,409,669 | 11/1968 | Dyke | 260/564 |
| 3,479,437 | 11/1969 | Szabo et al. | 424/304 |
| 3,547,951 | 12/1970 | Hardie et al. | 260/340.9 |
| 3,639,477 | 2/1972 | L'Italien | 260/564 A |
| 3,681,459 | 8/1972 | Hughes et al. | 424/326 |
| 3,769,427 | 10/1973 | Hughes et al. | 424/326 |
| 3,784,643 | 1/1974 | Suh et al. | 260/564 A |
| 3,803,324 | 4/1974 | Winter et al. | 424/326 |
| 3,804,898 | 4/1974 | Panneman | 260/564 A |
| 3,908,013 | 9/1975 | Hughes et al. | 424/258 |
| 3,949,089 | 4/1976 | Maxwell et al. | 424/326 |
| 3,968,243 | 7/1976 | Maxwell et al. | 424/326 |
| 3,975,533 | 8/1976 | Gauri | 117/54 |
| 3,976,643 | 8/1976 | Diamond et al. | 260/247.5 R |
| 3,976,787 | 8/1976 | Hughes et al. | 424/326 |
| 4,007,181 | 2/1977 | DuCharme et al. | 260/247.5 R |
| 4,014,934 | 3/1977 | Hughes et al. | 260/565 |
| 4,051,256 | 9/1977 | Swallow | 424/326 |
| 4,052,455 | 10/1977 | Matier et al. | 260/563 R |
| 4,060,640 | 11/1977 | Kodama et al. | 424/326 |
| 4,109,014 | 8/1978 | Liu et al. | 424/326 |
| 4,130,663 | 12/1978 | Matier et al. | 424/326 |
| 4,161,541 | 7/1979 | Rasmussen | 424/326 |
| 4,169,154 | 9/1979 | Cohen et al. | 424/322 |
| 4,393,077 | 7/1983 | Douglas et al. | 564/238 |
| 4,471,137 | 9/1984 | Barton et al. | 564/240 |
| 4,709,094 | 11/1987 | Weber et al. | 564/238 |
| 4,723,029 | 2/1988 | Vashi et al. | 560/13 |
| 4,742,054 | 5/1988 | Naftchi | 514/215 |
| 4,837,218 | 6/1989 | Olney | 514/646 |
| 4,891,185 | 1/1990 | Goldin | 422/69 |
| 4,898,978 | 2/1990 | Bergfield et al. | 564/231 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |
| 5,262,568 | 11/1993 | Weber et al. | 564/238 |
| 5,298,657 | 3/1994 | Durant | 564/238 |
| 5,308,869 | 5/1994 | Keana et al. | 514/637 |
| 5,312,840 | 5/1994 | Keana et al. | 514/634 |
| 5,336,689 | 8/1994 | Weber et al. | 514/634 |
| 5,385,946 | 1/1995 | Keana et al. | 514/634 |

FOREIGN PATENT DOCUMENTS

| | | |
|---|---|---|
| 0001500 | 4/1979 | European Pat. Off. . |
| 0035374 | 9/1981 | European Pat. Off. . |
| 0 147 537 | 7/1985 | European Pat. Off. . |
| 0179642 | 4/1986 | European Pat. Off. . |
| 514248 | 11/1930 | Germany . |
| 2029707 | 12/1970 | Germany . |
| 2133 056 | 1/1973 | Germany . |
| 2452691 | 5/1975 | Germany . |
| 3108564 | 11/1982 | Germany . |
| 223410 | 10/1924 | United Kingdom . |
| 224376 | 11/1924 | United Kingdom . |
| 258203 | 9/1926 | United Kingdom . |
| 478525 | 1/1938 | United Kingdom . |
| 1208252 | 10/1970 | United Kingdom . |
| WO 87/04433 | 7/1987 | WIPO . |
| WO 88/00583 | 1/1988 | WIPO . |
| WO 90/12575 | 11/1990 | WIPO . |
| WO 90/14067 | 11/1990 | WIPO . |
| WO 91/12797 | 9/1991 | WIPO . |
| WO 91/18868 | 12/1991 | WIPO . |
| WO 92/14697 | 9/1992 | WIPO . |
| WO 95/20950 | 8/1995 | WIPO . |

OTHER PUBLICATIONS

K. Ozeki et al., *Chemical and Pharmaceutical Bulletin*, 37(7):1780–1787 (1989).

A. Kreutzberger et al., *Archiv. Der Pharmazie*, 318:1043–1045 (1985).

Doull et al., A Survey of Compounds for Radiation Protection (USAF Radiation Laboratory).

D. Lloyd et al., Tetrahedron, 33:1379–1389 (1977).

H. Shimazu et al., Chemical Abstracts, 111 (2):16337m (1989).

T. Tada et al., Chemical Abstracts, 104(24):208252g (1986).

L. Kiselev et al., Chemical Abstracts, 91 (21):175291b (1979).

A. Heesing et al., Chemical Abstracts, 64(1):15776h (1966).
K. Akiba et al., Bull. Chem. Soc. Jap., 47(4):935–937 (1974).
Database Rtecs, "National Institute of Occupational Safety and Health", RTECS No. MF735000.
J. Keana et al., Proc. Natl. Acad. Sci., 86:5631–5635 (1989).
S. Siddiqui et al., Pakistan Journal of Scientific and Industrial Res., 30(3):163–181 (1987).
E. Maida et al., Wiener Klinische Wochenschrift, 90(2):43–48 (1978).
C. Chavkin et al., Advances in the Biosciences, 75:407–410 (1989).
P.N. Bhargava et al., Chemical Abstracts, 86:598, 189787b (1977).
H.W. Geluk et al., J. Med. Chem., 12:712–715B (1969).
M.W. Scherz et al., J. Med. Chem., 33:2421–2429 (1990).
A.A. Stolyarchuk et al., Chemical Abstracts, 86:522–523, 121071h (1977).
T.J.R. Weakley et al., Acta. Cryst., 46:2234–2236 (1990).
J.T. Adams et al., Eur. J. Pharm., 142:61–71 (1987).
B.G. Campbell et al., J. Neurosci., 9:3380–3391 (1989).
G.J. Durant et al., J. Med. Chem., 28:1414–1422 (1985).
M.P. Kavanaugh et al., Proc. Natl. Acad. Sci. USA, 85:2844–2848 (1988).
B. Tester et al., Society for Neuroscience, 19th Annual Meeting, 983, 396.17 (1989).
E. Weber et al., Proc. Natl. Acad. Sci. USA, 83:8784–8788 (1986).
C.A. Maryanoff et al., J. Org. Chem., 51:1882–1884 (1986).
S.R. Safir et al., J. Org. Chem., 13:924–932 (1948).
F.R. Sharp et al., Society for Neuroscience Abstr., 18, Abstr. No. 482.3 (1992).
B. Clement et al., Xenobiotica, 23(2):155–167 (1993).
Kiselev et al., Chemical Abstracts, vol. 66 (1967).
B. Bean, Ann. N.Y. Acad. Sci., 560:334–345 (1989).
B. Bean, Annu. Rev. Physiol., 51:367–384 (1989).
Bent et al., Pesticides, 74:63479m (1971).
Chernevskaya et al., Nature, 349:418–420 (1991).
D. Choi, Journal of Neuroscience, 10(8):2493–2501 (1990).
D. Choi, Cerebrovascular and Brain Metabolism Reviews, 2:105–147 (1990).
D. Choi, Neuron, 1:623–634 (1988).
Dreyer et al., Science, 248:364–367 (1990).
Durant et al., J. Med. Chem. 9:22–27 (1996).
Fox et al., J. Physiol., 394:149–172 (1987).
Fox et al., J. Physiol., 394:173–200 (1987).
Ginsburg et al., Chemical Abstracts, 4518 (1962).
Ginsburg et al., Zhurnal Organicheskoi Khimii, 7(11):2267–2270, Unverified Translation (1971).
Godfraind et al., Trends in Pharmacological Sciences, 10(8):297–301 (1989).
S. Goldin et al., Synthetic Neuroprotective Glutamate Release Blockers, Small Business Innovation Research Program Phase I Grant Application, funded Dec. 1991.
L. Heinisch, Journal f. prakt. Chemie, 329:290–300 (1987).
Huisgen et al., Chem. Ber., 98:1476–1486 (1965).
Huisgen et al., Chem. Abstracts, 63:2975 (1965).
Kaneko et al., Arzneim. Forsch./Drug. Res., 39(1):445–450 (1989).
Katragadda et al., Soc. for Neurosci. Abstr., 16:64 (1990).
Kreutzberger et al., Arch. Pharmz. Ber. Deut. Pharm. Ges., 305:400–405 (1972).
Kroeger et al., Chem. Abstr., 60:9264 (1964).
Kroger et al., Ber., 97:396–404 (1964).
Langlais et al., J. Neuroscience, 10(5):1664–1674 (1990).
Lemos et al., Neuron, 2:1419–1426 (1989).
Leung et al., Neuron, 3:767–772 (1989).
Malgouris et al., J. Neuroscience, 9(11):3720–3727 (1989).
B. Meldrum, Cerebrovascular and Brain Metabolism Reviews, 2:27–57 (1990).
Miura et al., Chem. Abstr., 109:75455d (1988).
Plaitakis et al., Science, 216:193–196 (1982).
Plummer et al., Neuron, 2:1453–1463 (1989).
Podrebarac et al., J. Med. Chem., 6:283–288 (1963).
Prasad et al., Can. J. Chem., 45:2247–2252 (1967).
Price et al., Soc. Neuroscience Abstracts, 16:377 (1990).
Sah et al., Soc. Neuroscience Abstr., 15:823 (1989).
Sasaki et al., Synthesis November, (11):718–719 (1975).
Subbarao et al., Soc. for Neurosci. Abstr., 15:601 (1989).
Sunderdiek et al., Chemical Abstracts, 81:91438k (1974).
J.B. Suszkiw, NATO ASI Series, H21:285–291 (1988).
Turner et al., Soc. Neurosci. Abstr., 16:1014 (1990).
Turner et al., Biochemistry, 28:586–593 (1989).
Turner et al., Analytical Biochemistry, 178:8–16 (1989).
Turner et al., Journal of Neuroscience, 5(3):841–849 (1985).
Vasilev et al., Chemical Abstract, 93:1500095u (1980).
Ahmad et al., Chemical Abstract, 108:221382 (1988).

*Primary Examiner*—Peter O'Sullivan
*Attorney, Agent, or Firm*—David G. Conlin; Peter F. Corless; Dike, Bronstein, Roberts & Cushman, LLP

[57] ABSTRACT

The present invention provides therapeutically useful substituted guanidines and methods of treatment and pharmaceutical compositions that utilize or comprise one or more of such guanidines.

9 Claims, No Drawings

THERAPEUTIC SUBSTITUTED GUANIDINES

This is a continuation of International Application PCT/US94/13245, with an international filing date of Nov. 22, 1994, now abandoned, and a continuation-in-part of U.S. application Ser. No. 08/156,773, filed Nov. 23, 1993, now abandoned.

BACKGROUND OF THE INVENTION

1. Field of the Invention

The present invention relates to certain substituted guanidines, pharmaceutical compositions and methods of treatment that comprise such guanidines.

2. Background Art

A number of substituted guanidines have been reported. See, e.g., U.S. Pat. Nos. 1,411,731, 1,422,506, 1,597,233,. 1,642,180, 1,672,431, 1,730,388, 1,756,315, 1,795,739, 1,850,682, 2,145,214, 2,254,009, 2,633,474, 3,117,994, 3,140,231, 3,159,676, 3,228,975, 3,248,426, 3,252,816, 3,283,003, 3,270,054, 3,301,755, 3,320,229, 3,301,775, 3,409,669, 3,479,437, 3,547951, 3,639,477, 3,681,457, 3,769,427, 3,784,643, 3,803,324, 3,908,013, 3,949,089, 3,975,533, 3,976,787, 4,060,640, 4,014,934, 4,161,541, 4,709,094, 4,906,779, 5,093,525, and 5,190,976; PCT applications WO 90/12575, WO 91/12797, WO 91/18868, and WO 92/14697; and H.W. Geluk, et al., *J. Med. Chem.*, 12:712 (1969).

The amino acid L-glutamate is widely thought to act as a chemical transmitter substance at excitatory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisqualic acid and N-methyl-D-aspartic acid, respectively. An amino acid which activates one or more of these receptor types is referred to as an excitatory amino acid (EAA).

The NMDA subtype of excitatory amino acid receptors is activated during normal excitatory synaptic transmission in the brain. Activation of NMDA receptors under normal conditions is responsible for the phenomena of long-term potentiation, a memory-like phenomenon, at excitatory synapses. Excessive excitation of neurons occurs in epileptic seizures and it has been shown that overactivation of NMDA receptors contributes to the pathophysiology of epilepsy.

NMDA receptors are also strongly involved in nerve cell death which occurs following brain or spinal cord ischemia. Upon the occurrence of ischemic brain insults such as stroke or heart attack, an excessive release of endogenous glutamate occurs, resulting in the over-stimulation of NMDA receptors. Associated with the NMDA receptors is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor, plays an important role in nerve cell death. See, e.g., S. M. Rothman, et al., *Trends in Neurosci.*, 10(7):299–302 (1987).

Agents which block responses to NMDA receptor activation therefore have therapeutic uses in the treatment of neurological disorders such as epilepsy and also in the prevention of nerve cell death resulting from hypoxia or hypoglycemia or following brain ischemia which occurs during stroke, trauma and heart attack. A number of disorders of the nervous system are associated with neurodegeneration that may be caused by overactivation of NMDA receptors. Antagonists of NMDA receptor-mediated responses have potential therefore for the treatment of such disorders as Alzheimer's disease, Parkinson's disease, Huntington's disease, Amyotrophic Lateral Sclerosis, Down's Syndrome and Korsakoff's disease.

Research on the NMDA receptor-ion channel complex has led to determination of a receptor site within the ion channel known as the PCP receptor. See J. P. Vincent, et al., *Proc. Natl. Acad. Sci. USA*, 76:4678–4682 (1979); S. R. Zukin, et al., *Proc. Natl. Acad. Sci. USA*, 76:5372–5376 (1979); M. S. Sonders, et al., *Trends in Neurosci.*, 11(1):37–40 (1988); and N. A. Anis, et al., *Br. J. Pharmacol.*, 79:565–575 (1983). A compound which binds to the PCP receptor can act as an ion channel blocker, thereby interrupting the flow of ions through the cell membrane. In this manner, agents which interact with the PCP receptor act as non-competitive antagonists reducing the agonist action of glutamate at the NMDA receptor.

Known PCP receptor ligands include PCP, i.e., Phencyclidine, analogs such as 1-[1-(2-thienyl)-cyclohexyl]-piperidine (TCP), benzomorphan (sigma) opiates, and (+)-5-methyl-10,11-dihydro-5H-dibenzo[a,d]cycloheptene-5,10-imine (i.e., the drug MK-801, see U.S. Pat. No. 4,399,141). See, also, E. H .F. Wong, et al., *Proc. Natl. Acad. Sci. USA*, 83:7104–7108 (1986), and W. J. Thompson, et al., *J. Med. Chem.*, 33:789–808 (1990).

SUMMARY OF THE INVENTION

The present invention provides substituted guanidines of Formula I:

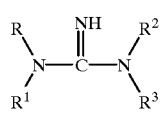

wherein R, $R^1$ and $R^2$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted thioalkyl having from 1 to about 20 carbon atoms, substituted or unsubstituted aminoalkyl having from 1 to about 20 carbon atoms, substituted or unsubstituted carbocyclic aryl having at least about 6 ring carbon atoms, substituted or unsubstituted aralkyl having at least about 6 carbon ring atoms, or a substituted or unsubstituted heteroaromatic or heteroalicyclic group having from 1 to 3 rings, 3 to 8 ring members in each ring and from 1 to 3 hetero atoms, and at least one of said R and $R^1$ groups being other than hydrogen;

$R^3$ is a carbocyclic aryl having at least 6 ring carbon atoms and independently substituted at one or more ring positions, preferably 1 to 3 ring positions, by moieties of haloalkyl having from 1 to about 20 carbon atoms, substituted or unsubstituted thioalkyl having from 1 to about 3 carbon atoms including halothioalkyl, substituted or unsubstituted alkylsulfinyl having from 1 to about 20 carbon atoms, substituted or unsubstituted alkylsulfinyl having from 1 to about 20 carbon atoms, and haloalkoxy having from 1 to about 20 carbon atoms; and pharmaceutically acceptable salts thereof; with the exclusion of N-(1-naphthyl)-N'-(3-trifluoromethylphenyl)-N'-methylguanidine, N-(1-naphthyl)-N'-(3-trifluoromethylphenyl)-N'-ethylguanidine, N-(8-coumarinyl)-N'-(3-trifluoromethylphenyl)-N'-methylguanidine, and N-(8-coumarinyl)-N'-(3-trifluoromethylphenyl)-N'-ethylguanidine, and the proviso that $R^3$ is not substituted by trifluoromethyl when one of said R and $R^1$ groups is hydrogen and $R^2$ is hydrogen.

Preferred compounds of Formula I include those compounds where $R^3$ is phenyl. More preferred are those compounds where $R^3$ is monosubstituted phenyl, i.e. where $R^3$ is phenyl with four aromatic hydrogens and a single non-hydrogen ring substituent. Still more preferred is where $R^3$ is phenyl monosubstituted at the 3-position. Tri-substituted compounds of Formula I (i.e., where only two of said R, $R^1$ and $R^2$ groups are other than hydrogen) and tetra-substituted compounds of Formula I (i.e., where each of said R, $R^1$ and $R^2$ groups are other than hydrogen) are generally preferred compounds. Also preferred are those compounds where at least one of R and $R^1$ is a substituted or unsubstituted carbocyclic aryl group such as substituted or unsubstituted phenyl or naphthyl, particularly where $R^1$ and/or $R^2$ is substituted or unsubstituted alkyl.

Preferred compounds of Formula I exhibit a high affinity for the PCP receptor. The phrase "high affinity for the PCP receptor" as used herein means the compound exhibits an $IC_{50}$ of 1 μM or less in a typical PCP receptor binding assay such as described in Example 7 which follows.

The substituted guanidines of the invention are useful for a number of therapeutic applications. Accordingly, the present invention includes methods for treatment and/or prophylaxis of neurological conditions such as epilepsy, neurodegenerative conditions and/or nerve cell death resulting from e.g. hypoxia, hypoglycemia, brain or spinal chord ischemia, brain or spina chord trauma such as from stroke, and the like. Compounds of Formula I also are useful to treat and/or prevent various neurodegenerative diseases such as Parkinson's disease, Huntington's disease, Amyotrophic Lateral Sclerosis, Alzheimer's disease, Down's Syndrome and Korsakoff's disease. The methods of the invention in general comprise administration of a therapeutically effective amount of one or more compounds of Formula I to an animal, including a mammal, particularly a human.

The invention also provides pharmaceutical compositions that comprise one or more compounds of Formula I and a suitable carrier.

DETAILED DESCRIPTION OF THE INVENTION

In one aspect the present invention provides substituted guanidines of Formula I:

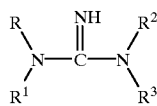

I wherein R, $R^1$ and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted thioalkyl, substituted or unsubstituted aminoalkyl, substituted or unsubstituted carbocyclic aryl having at least about 6 ring carbon atoms, substituted or unsubstituted aralkyl having at least about 6 carbon ring atoms, or a substituted or unsubstituted heteroaromatic or heteroalicyclic group having from 1 to 3 rings, 3 to 8 ring members in each ring and from 1 to 3 hetero atoms, and at least one of said R and $R^1$ groups being other than hydrogen;

$R^3$ is a carbocyclic aryl having at least 6 ring carbon atoms and independently substituted at one or more ring positions by haloalkyl, substituted or unsubstituted thioalkyl having from 1 to about 3 carbon atoms including halothioalkyl, substituted or unsubstituted alkylsulfinyl, substituted or unsubstituted alkylsulfinyl, or haloalkoxy, and pharmaceutically acceptable salts thereof; with the exclusion of N-(1-naphthyl)-N'-(3-trifluoromethylphenyl)-N'-methylguanidine, N-(1-naphthyl)-N'-(3-trifluoromethylphenyl)-N'-ethylguanidine, N-(8-coumarinyl)-N'-(3-trifluoromethylphenyl)-N'-methylguanidine, and N-(8-coumarinyl)-N'-(3-trifluoromethylphenyl)-N'-ethylguanidine, and the proviso that $R^3$ is not substituted by trifluoromethyl when one of said R and $R^1$ groups is hydrogen and $R^2$ is hydrogen. Compounds excluded by said proviso include N-(1-naphthyl)-N'-(3-trifluoromethylphenyl) guanidine and N-(trifluoromethylphenyl)-N'-(ethylphenyl)guanidine.

Typically preferred compounds of Formula I are compounds of the following Formula Ia:

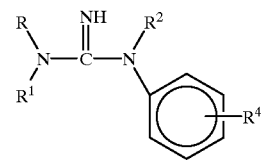

wherein R, $R^1$ and $R^2$ are the same as defined above for Formula I, and $R^4$ is haloalkyl having from 1 to about 20 carbon atoms, substituted or unsubstituted thioalkyl having from 1 to about 3 carbon atoms including halothioalkyl, substituted or unsubstituted alkylsulfinyl having from 1 to about 20 carbon atoms, substituted or unsubstituted alkylsulfinyl having from 1 to about 20 carbon atoms, or haloalkoxy having from 1 to about 20 carbon atoms; and pharmaceutically acceptable salts thereof; with the exclusion of N-(1-naphthyl)-N'-(3-trifluoromethylphenyl)-N'-methylguanidine, N-(1-naphthyl)-N'-(3-trifluoromethylphenyl)-N'-ethylguanidine, N-(8-coumarinyl)-N'-(3-trifluoromethylphenyl)-N'-methylguanidine, and N-(8-coumarinyl)-N'-(3-trifluoromethylphenyl)-N'-ethylguanidine, and the proviso that $R^4$ is not trifluoromethyl when one of said R and $R^1$ groups is hydrogen and $R^2$ is hydrogen. Still more preferred are those compounds of the above Formula Ia where the depicted phenyl ring is meta-substituted by the $R^4$ group.

In another aspect of the invention, compounds of the invention include those as defined by the above Formulas I or Ia but with the further proviso that $R^3$ is not substituted by, or $R^4$ is not fluoroalkyl including trifluoromethyl. In a still further aspect, compounds of the invention include those as defined by the above Formulas I or Ia but with the further proviso that $R^3$ is not substituted by, or $R^4$ is not haloalkyl.

Particularly preferred compounds of Formula I and Ia include those compounds where R is substituted or unsubstituted carbocyclic aryl, particularly substituted or unsubstituted phenyl or naphthyl, and $R^1$ and $R^2$ are independently hydrogen or alkyl such as methyl, ethyl or propyl.

Suitable halogen substituent groups of compounds of Formula I include F, Cl, Br and I. Alkyl groups of compounds of Formula I preferably have from 1 to about 12 carbon atoms, more preferably 1 to about 8 carbon atoms, still more preferably 1 to about 6 carbon atoms, even more preferably 1, 2, 3 or 4 carbon atoms. Methyl, ethyl and propyl including isopropyl are particularly preferred alkyl groups. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups. Preferred alkenyl and alkynyl groups of compounds of Formula I have one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The terms alkenyl and alkynyl as used herein refer to both cyclic and noncyclic groups, although straight or branched noncyclic groups are generally more preferred. Preferred alkoxy groups of compounds of Formula I include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. With regards to R, $R^1$ and $R^2$ substituents, preferred thioalkyl groups include those groups having one or more thioether linkages and from 1 to about 12 carbon atoms, more preferably from 1 to about 8 carbon atoms, and still more preferably 1 to about 6 carbon atoms. Particularly preferred are thioalkyl groups having 1, 2, 3 or 4 carbon atoms. Preferred aminoalkyl groups include those groups having one or more primary, secondary and/or tertiary amine groups, and from 1 to about 12 carbon atoms, more preferably one to about 8 carbon atoms, still more preferably 1 to about 6 carbon atoms, even more preferably 1, 2, 3 or 4 carbon atoms. Secondary and tertiary amine groups are generally more preferred than primary amine moieties. Suitable heteroaromatic groups of compounds of Formula I contain N, O and/or S heteroatoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups of compounds of Formula I contain heteroatoms of N, O and/or S and include, e.g., tetrahydrofuranyl, tetrahydropyranyl, piperidinyl, morpholino and pyrrolindinyl groups. Suitable carbocyclic aryl groups of compounds of Formula I include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including 2,5-substituted phenyl, 2,4,5-substituted phenyl and 3-substituted phenyl; naphthyl including 1-naphthyl and 2-naphthyl; biphenyl; phenanthryl; and anthracyl. Suitable aralkyl groups of compounds of Formula I include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl ($-CH_2$-naphthyl).

Preferred $R^3$ and $R^4$ haloalkyl aryl ring substituents have one or more F, Cl, Br, or I atoms, more preferably one or more F, Cl or Br atoms, and from 1 to about 12 carbon atoms, more preferably 1 to about 8 carbon atoms, still more preferably 1 to about 6 carbon atoms, even more preferably 1, 2, 3 or 4 carbon atoms. Groups containing one or more fluorine atoms are particularly preferred. Methyl and ethyl halo-substituted groups are also preferred, particularly fluoro-substituted methyl and ethyl groups. Fluoroethyl and fluoromethyl, including trifluoromethyl, are especially preferred $R^3$ and $R^4$ haloalkyl groups.

Preferred $R^3$ and $R^4$ haloalkoxy ring substituents have one or more F, Cl, Br, or I atoms, one or more oxygen linkages, and from 1 to about 12 carbon atoms, more preferably one to about 8 carbon atoms, still more preferably 1 to about 6 carbon atoms, even more preferably 1, 2, 3 or 4 carbon atoms. Methoxy and ethoxy halo-substituted groups are particularly preferred. F, Cl and Br are more preferred halogens of such haloalkoxy groups, with F being particularly preferred. Fluoroethoxy and fluoromethoxy, including trifluoromethoxy, 2-trifluoroethoxy ($CF_3CH_2O$) and pentafluoroethoxy, are especially preferred haloalkoxy groups.

Methylthio ($-SCH_3$) and ethylthio ($-SCH_2CH_3$) are particularly preferred $R^3$ and $R^4$ thioalkyl ring substitutents. Halothioalkyl groups are particularly preferred substituted thioalkyl $R^3$ and $R^4$ groups and contain one or more F, Cl, Br or I atoms, preferably one or more F, Cl or Br atoms, more preferably one or more F atoms, and preferably have 1 or 2 carbon atoms. Fluoromethylsulfide, particularly trifluoromethylsulfide ($-SCF_3$), and fluoroethylsulfide such as 2-trifluoroethylsulfide ($-SCH_2CF_3$) and pentafluoroethylsulfide ($-SCF_2CF_3$), are particularly preferred $R^3$ and $R^4$ halothioalkyl groups. Preferred compounds also include those of Formula Ia where $R^4$ is thioalkyl such as e.g. methylthio or ethylthio, and R is phenyl substituted by halogen or alkyl such as $C_{1-3}$ alkyl, or R is phenyl substituted by thioalkyl such as e.g. ethylthio or methylthio.

Preferred $R^3$ and $R^4$ alkylsulfinyl aryl ring substituents have one or more sulfoxide groups, more typically one sulfoxide group, and from 1 to about 12 carbon atoms, more preferably 1 to about 8 carbon atoms, still more preferably 1 to about 6 carbon atoms, even more preferably 1 to about 3 carbon atoms. Methylsulfinyl ($-S(O)CH_3$) and ethylsulfinyl ($-S(O)CH_2CH_3$) are particularly preferred $R^3$ and $R^4$ alkylsulfinyl groups. Preferred substituted alkylsulfinyl groups include haloalkylsulfinyl groups that contain one or more F, Cl, Br or I atoms, preferably one or more F atoms, and preferably 1 to about 3 carbon atoms, more preferably one or two carbon atoms. Specifically preferred groups include fluoromethylsulfinyl, particularly trifluoromethylsulfinyl ($-S(O)CF_3$), and fluoroethylsulfinyl such as 2-trifluoroethylsulfinyl ($-S(O)CH_2CF_3$) and pentafluoroethylsulfinyl ($-S(O)CF_2CF_3$).

Preferred $R^3$ and $R^4$ alkylsulfinyl ring substituents have one or more sulfono ($SO_2$) groups, more typically one sulfono group, and from 1 to about 12 carbon atoms, more preferably 1 to about 8 carbon atoms, still more preferably 1 to about 6 carbon atoms, even more preferably 1 to about 3 carbon atoms. Methylsulfinyl ($-S(O)_2CH_3$) and ethylsulfinyl ($-S(O)_2CH_2CH_3$) are particularly preferred $R^3$ and $R^4$ sulfonoalkyl groups. Preferred substituted alkylsulfinyl groups include haloalkylsulfinyl groups that contain one or more F, Cl, Br or I atoms, preferably one or more F atoms, and preferably 1 to about 3 carbon atoms, more preferably one or two carbon atoms. Specifically preferred groups include fluoromethylsulfinyl, particularly trifluoromethylsulfinyl ($-S(O)_2CF_3$), and fluoroethylsulfinyl such as 2-trifluoroethylsulfinyl ($-S(O)_2CH_2CF_3$) and pentafluoroethylsulfinyl ($-S(O)_2CF_2CF_3$).

Without wishing to be bound by theory, compounds of the invention where $R^3$ or $R^4$ substituents contain an alkylsulfinyl and/or alkylsulfinyl group, may be, in effect, "pro-drugs" wherein after administration of the compound to a subject the sulfinyl or sulfinyl group(s) are metabolized (reduced) in vivo to the corresponding sulfide moiety.

Said substituted R, $R^1$, $R^2$, $R^3$ and $R^4$ groups may be substituted at one or more available positions by one or more suitable groups such as, e.g., halogen such as fluoro, chloro, bromo and iodo; cyano; hydroxyl; nitro; azido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon atoms or from 2 to about 6 carbon atoms; alkoxy groups having those having one or more oxygen linkages and from 1 to about 12 carbon atoms or 1 to about 6 carbon atoms; thioalkyl groups including those moieties having one or more thioether linkages and from 1 to about 12 carbon atoms or from 1 to about 6 carbon atoms; and aminoalkyl groups such as groups having one or more N atoms and from 1 to about 12 carbon atoms or from 1 to about 6 carbon atoms.

It should be understood that alkoxy, haloalkoxy, thioalkyl, alkylsulfinyl, alkylsulfinyl and aminoalkyl substituent groups described above include groups where a hetero atom is directly bonded to a ring system, such as a carbocyclic aryl group or a heterocyclic group, as well as groups where a hetero atom of the group is spaced from such ring system by an alkylene linkage, e.g. of 1 to about 4 carbon atoms.

Specifically preferred compounds of Formula I include:

N-(1-naphthyl)-N'-(3-methylthiophenyl)-N'-methylguanidine;
N-(1-naphthyl)-N-methyl-N'-(3-methylthiophenyl)guanidine;
N-(1-naphthyl)-N,N'-dimethyl-N'-(3-methylthiophenyl)guanidine;
N-(1-naphthyl)-N'-(3-methylthiophenyl)guanidine;
N-(1-naphthyl)-N'-(3-methylsulfinylphenyl)-N'-methylguanidine;
N-(1-naphthyl)-N-methyl-N'-(3-methylsulfinylphenyl)guanidine;
N-(1-naphthyl)-N,N'-dimethyl-N'-(3-methylsulfinyiphenyl)guanidine;
N-(1-naphthyl)-N'-(3-methylsulfinylphenyl)guanidine;
N-(1-naphthyl)-N'-(3-methylsulfinylphenyl)-N'-methylguanidine;
N-(1-naphthyl)-N-methyl-N'-(3-methylsulfinylphenyl)guanidine;
N-(1-naphthyl)-N,N'-dimethyl-N'-(3-methylsulfinylphenyl)guanidine;
N-(1-naphthyl)-N'-(3-methylsulfinylphenyl)guanidine;
N-(1-naphthyl)-N'-(3-trifluoromethylthiophenyl)-N'-methylguanidine;
N-(1-naphthyl)-N-methyl-N'-(3-trifluoromethylthiophenyl)guanidine;
N-(1-naphthyl)-N,N'-dimethyl-N'-(3-trifluoromethylthiophenyl)guanidine;
N-(1-naphthyl)-N'-(3-trifluoromethylthiophenyl)guanidine;
N-(1-naphthyl)-N'-(3-pentafluoroethylphenyl)-N'-methylguanidine;
N-(1-naphthyl)-N-methyl-N'-(3-pentafluoroethylphenyl)guanidine;
N-(1-naphthyl)-N,N'-dimethyl-N'-(3-pentafluoroethylphenyl)guanidine;
N-(1-naphthyl)-N'-(3-pentafluoroethylphenyl)guanidine;
N-(1-naphthyl)-N'-(3-trifluoromethoxyphenyl)-N'-methylguanidine;
N-(1-naphthyl)-N-methyl-N'-(3-trifluoromethoxyphenyl)guanidine;
N-(1-naphthyl)-N-N'-dimethyl-N'-(3-trifluoromethoxyphenyl)guanidine;
N-(1-naphthyl)-N'-(3-trifluoromethoxyphenyl)guanidine;
N-(3-ethylphenyl)-N'-(3-methylthiophenyl)-N'-methylguanidine;
N-(3-ethylphenyl)-N-methyl-N'-(3-methylthiophenyl)guanidine;
N-(3-ethylphenyl)-N,N'-dimethyl-N'-(3-methylthiophenyl)guanidine;
N-(3-ethylphenyl)-N'-(3-methylthiophenyl)guanidine;
N-(3-ethylphenyl)-N'-(3-methylsulfinylphenyl)-N'-methylguanidine;
N-(3-ethylphenyl)-N-methyl-N'-(3-methylsulfinylphenyl)guanidine;
N-(3-ethylphenyl)-N,N'-dimethyl-N'-(3-methylsulfinylphenyl)guanidine;
N-(3-ethylphenyl)-N'-(3-methylsulfinylphenyl)guanidine;
N-(3-ethylphenyl)-N'-(3-methylsulfinylphenyl)-N'-methylguanidine;
N-(3-ethylphenyl)-N-methyl-N'-(3-methylsulfinylphenyl)guanidine;
N-(3-ethylphenyl)-N,N'-dimethyl-N'-(3-methylsulfinylphenyl)guanidine;
N-(3-ethylphenyl)-N'-(3-methylsulfinylphenyl)guanidine;
N-(3-ethyl phenyl)-N'-(3-trifluoromethylthiophenyl)-N'-methylguanidine;
N-(3-ethylphenyl)-N-methyl-N'-(3-trifluoromethylthiophenyl)guanidine;
N-(3-ethylphenyl)-N,N'-dimethyl-N'-(3-trifluoromethylthiophenyl) guanidine;
N-(3-ethylphenyl)-N'-(3-trifluoromethylthiophenyl) guanidine;
N-(3-ethylphenyl)-N'-(3-pentafluoroethylphenyl)-N'-methylguanidine;
N-(3-ethylphenyl)-N-methyl-N'-(3-pentafluoroethylphenyl)guanidine;
N-(3-ethylphenyl)-N,N'-dimethyl-N'-(3-pentafluoroethylphenyl)guanidine;
N-(3-ethylphenyl)-N'-(3-pentafluoroethylphenyl)guanidine;
N-(3-ethylphenyl)-N'-(3-trifluoromethoxyphenyl)-N'-methylguanidine;
N-(3-ethylphenyl)-N-methyl-N'-(3-trifluoromethoxyphenyl)guanidine;
N-(3-ethylphenyl)-N,N'-dimethyl-N'-(3-trifluoromethoxyphenyl)guanidine;
N-(3-ethylphenyl)-N'-(3-trifluoromethoxyphenyl) guanidine;
N-(3-methylthiophenyl)-N'-(3-methylthiophenyl)guanidine;
N-(3-methylthiophenyl)-N'-(3-methylthiophenyl)-N'-methylguanidine;
N-(3-methylthiophenyl)-N-methyl-N'-(3-methylthiophenyl) guanidine;
N-(3-methylthiophenyl)-N,N'-dimethyl-N'-(3-methylthiophenyl)guanidine;
N-(3-methylthiophenyl)-N'-(3-bromophenyl)guanidine;
N-(3-methylthiophenyl)-N'-(3-bromophenyl)-N'-methylguanidine;
N-(3-methylthiophenyl)-N-methyl-N'-(3-bromophenyl)guanidine;
N-(3-methylthiophenyl)-N,N'-dimethyl-N'-(3-bromophenyl)guanidine; and pharmaceutically acceptable salts of said compounds.

In another aspect, preferred compounds include, particularly for use in the methods of therapeutic treatment disclosed herein, N-(3-ethylphenyl)-N,N'-dimethyl(3-trifluoromethylphenyl)guanidine; N-(3-ethylphenyl)-N-methyl-N'-(3-trifluoromethylphenyl)guanidine; N-(3-ethylphenyl)-N'-(3-trifluoromethylphenyl)-N'-methylguanidine; N-(1-naphthyl)-N'-(3- trifluoromethylphenyl)-N-methylguanidine; and N-(1-naphthyl)-N'-(3-trifluoromethylphenyl)-N,N'-dimethylguanidine; and pharmaceutically acceptable salts thereof.

Compounds of Formula I can be readily prepared by the reaction of an amine, typically an amine salt such as an amine hydrochloride, with a preformed alkyl or aryl cyanamide (see S. R. Safer, et al., *J. Org. Chem.*, 13:924 (1948)) or the corresponding N-substituted alkyl or aryl cyanamide. This is a particularly suitable method for producing N,N'-diaryl-N'-alkyl guanidines in which the substituents are not identical. For a synthesis of asymmetrical guanidines, see G. J. Durant, et al., *J. Med. Chem.*, 28:1414 (1985), and C. A. Maryanoff, et al., *J. Org. Chem.*, 51:1882 (1986), incorporated by reference herein. For additional discussion of guanidine synthesis, see PCT application WO 91/12797 and U.S. Pat. No. 5,093,525, incorporated by reference herein. See also H. W. J. Cressman, *Org. Syn. Coll.*, 3:608–609 (1955); M. P. Kavanaugh, et al., *Proc. Natl. Acad. Sci. USA*, 85:2844–2848 (1988); and E. Weber, et al., *Proc. Natl. Acad. Sci. USA*, 83:8784–8788 (1986), all incorporated herein by reference.

More particularly, compounds of Formula I can be prepared suitably by reaction of an appropriate amine salt such an amine hydrochloride with a slight molar excess (e.g., ca. 1.1 molar equivalent) of a substituted cyanamide in a suitable solvent such as toluene or chlorobenzene under an inert atmosphere such as argon or nitrogen. The reaction solution is then heated from about 110° to 120° C. for 2 to about 16 hours until reaction completion, e.g. as indicated by thin layer chromatography. The reaction solution is then cooled to room temperature, and then preferably diluted with a solvent such as absolute alcohol. The solvent is then removed under reduced pressure to provide the desired substituted guanidine. The crude product then can be purified by recrystallization and/or flash chromatography, e.g. by elution on silica gel (60–200 mesh, 50x w/w) with 5–25% methanol in ethyl acetate. Suitable recrystallization solvents include an ethanol/ethyl acetate mixture and an ethanol/ether mixture. The cyanamide and amine reagents with appropriate substituents (i.e., R, $R^1$, $R^2$, $R^3$, $R^4$ groups) are commercially available or can be readily prepared by known procedures. For example, the cyanamide starting material can be synthesized from the correspondingly substituted amine by treatment with cyanogen bromide (BrCN) in suitable solvent such as dry ethyl ether. The amine hydrochloride can be obtained by treatment of an appropriate amine with an excess of HCl. For example, a substituted aniline hydrochloride salt can be prepared by adding methanolic HCl to a cooled solution of the substituted aniline and then stirring at room temperature for about 30 minutes.

As discussed above, the present invention includes methods for treating or preventing certain neurological disorders, including the consequences of stroke or traumatic brain injury, epilepsy or neurodegenerative diseases comprising the administration of an effective amount of one or more guanidines of Formula I to a subject including a mammal, particularly a human, in need of such treatment.

Further provided are methods of ameliorating the neurotoxic effect induced by glutamate interacting with the NMDA receptor of a nerve cell, comprising administering to a subject, such as a mammal, particularly a human, exhibiting symptoms of or susceptible to such neurotoxic effect, one or more compounds of Formula I in an amount effective to ameliorate the neurotoxic effect.

This invention also provides methods of inhibiting NMDA receptor-ion channel related neurotoxicity comprising administering to a subject such as a mammal, particularly a human, one or more compounds of Formula I in an amount effective to inhibit the neurotoxicity.

The invention further provides a method of treating Korsakoff's disease, a chronic alcoholism-induced condition, comprising administering to a subject including a mammal, particularly a human, one or more compounds of Formula I in an amount effective to treat the disease. Pretreatment of animals with the NMDA antagonist MK-801 (Merck Index, monograph 3392, 11th ed., 1989) markedly attenuates the extent of cell loss, hemorrhages and amino acid changes in a rat model of Korsakoff's disease. See P. J. Langlais, et al., *Soc. Neurosci. Abstr.*, 14:774 (1988). Therefore, compounds of the present invention have utility for the attenuation of cell loss, hemorrhages and amino acid changes associated with Korsakoff's disease.

Certain pharmacological activity of compounds of Formula I can be determined by, e.g., a method involving: (a) determining the binding affinity with respect to the PCP receptor by competitive displacement of tritiated MK-801; (b) in vitro cytotoxicity studies measuring the ability of the compound to prevent nerve cell death caused by exposure to glutamate; and (c) determination of in vivo neuroprotective ability using animal models.

Evaluation of the binding activity of compounds of Formula I with respect to the PCP receptor is suitably performed using radioligand binding assays. The compounds are tested to determine their ability to displace tritiated MK-801 which is used to label PCP receptors. Evaluating the competitive displacement binding data, the preferred compounds are those which exhibit a high affinity (i.e., low $IC_{50}$ value) for the PCP receptors. Under such PCP binding activity studies, an $IC_{50}$ value of at most about 1 $\mu$M, preferably at most about 0.5 $\mu$M, indicates a high binding affinity.

Compounds of Formula I may be used in therapy in conjunction with other medicaments. For example, for treatment of a stroke victim, one or more compounds of Formula I may be suitably administered together with a pharmaceutical targeted for interaction in the blood clotting mechanism such as strepo-kinase, TPA and urokinase.

As discussed above, preferred guanidines of Formula I exhibit high affinity for the PCP receptor. Thus, in addition to the treatment of neurodegeneration and related conditions discussed above, the guanidines of the present invention may also be used as a pharmacological tool in an animal model for the screening of potential PCP receptor ligands.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means. Guanidines of the present invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, etc.

The compounds of this invention can be employed, either alone or in combination with one or more other therapeutic agents as discussed above, as a pharmaceutical composition in mixture with conventional excipient, i.e., pharmaceutically acceptable organic or inorganic carrier substances suitable for oral parenteral, enteral or intranasal application which do not deleteriously react with the active compounds and are not deleterious to the recipient thereof. Pharmaceutical composition adapted for oral or parenteral administration are often preferred. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are preferred. The compounds of this invention are particularly valuable in the treatment of mammalian subjects, e.g., humans, wherein the pathophysiology of the disease involves excessive excitation of nerve cells by agonists of the NMDA receptor. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease. Also suitable for treatment are those subjects suffering from or likely to suffer from nervous system dysfunctions resulting from, for example, epilepsy or nerve cell degeneration which is the result of hypoxia, hypoglycemia, brain or spinal chord ischemia or brain or spinal chord trauma. Typical candidates for treatment include heart attack, stroke, brain or spinal cord injury patients, patients undergoing major surgery where brain ischemia is a potential complication and patients such as divers suffering from decompression sickness due to gas emboli in the blood stream.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of Formula I, particularly when using the more potent compound(s) of Formula I, will be in the range of from 0.01 to 20 milligrams per kilogram bodyweight of recipient per day, preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of Formula I per unit dosage, preferably from 0.2 to 2 milligrams per unit dosage.

As with prior guanidines such as those reported in U.S. Pat. No. 1,41 1,713, the guanidines of the present invention should have utility as rubber accelerators.

The entire text of all applications, patents and publications cited above and below are incorporated by herein.

The following non-limiting examples are illustrative of the invention.

GENERAL COMMENTS

In the following examples, melting points (mp) were determined in open capillary tubes on a Thomas-Hoover apparatus (compounds melting <230° C.) and are uncorrected. The NMR spectra of all compounds were recorded on a Bruker-300, and chemical shifts are reported in ppm relative to the residual signal of the deuterated solvent ($CHCl_3$, 7.26 ppm; $HCD_2OD$, 3.30 ppm; TMS, 0.00 ppm). IR spectra were recorded on a Nicolet 5DXB FT-IR, or a Perkin-Elmer model 1420 in $CHCl_3$ or neat. IR and NMR spectra of all compounds are consistent with their assigned structures. Elemental analyses were performed by M-H-W Laboratories (Phoenix, Ariz.), or Galbraith Laboratories (Knoxville, Tenn.). Chlorobenzene, 1-aminonaphthalene, 3-ethylaniline, BrCN, $CH_3I$, were obtained from Aldrich Chemical Co., and used as received. Bromcresol green spray reagent was purchased from Sigma Co. All solvents were HPLC or reagent grade. 1-naphthyl cyanamide that can be used to prepare compounds of the following examples is suitably prepared by the following procedure. To a solution of 20.0 g (140 mMol) 1-naphthylamine in either at 0° C. was added by cannulation a solution of 17.5 Ml (87.5 mMol) BrCN (5.0 M in $CH_3CN$; Aldrich). After 0.5 hours the cooling bath was removed and the mixture was stirred at room temperature overnight (14 hours). A crystalline precipitate of the amine.HBr was formed, which was filtered off under suction, and washed with ethyl acetate (15 ml×3). The filtrate was concentrated in vacuo to leave 12.5 g of a purple colored solid of the crude cyanamide, whose TLC showed the presence of minor amounts of the hydrobromide amine salt. The crude solid was stirred with water (200 ml) for 1 hour, after which filtration under suction left a pinkish solid which was dried in a vacuum oven overnight to afford 9.2 (78.3%) of the pure 1-naphthyl cyanamide. Other materials used in the following examples are suitably prepared by means described in the above mentioned documents such as WO 91/12797 and U.S. Pat. No. 5,093,525, and other known methods.

EXAMPLE 1

Preparation of N-(1-Naphthyl)-N'-(3-thiomethylphenyl)-N'-methylguanidine hydrochloride (Formula Ia: hydrochloride salt of R=1-naphthyl, $R^1$=H, $R^2$=$CH_3$, $R^4$=m—$SCH_3$)

A mixture of 0.168 g (4.71 mMol) 1-naphthyl cyanamide and 0.175 g (4.27 mMol) N-methyl-3-thiomethylaniline hydrochloride was heated in 15 mL toluene at 110–120° C. for about 3 hours. After cooling to ambient temperature, excess ether was added to the reaction mixture to completely precipitate the product, which was then filtered through a Buchner funnel and washed several times with ethyl acetate to remove colored impurities. The resultant residue was taken up in boiling ethanol, treated with Norit (declorizing charcoal) for 0.5 hours and then filtered through Celite. The filtrate was concentrated to obtain a solid which on recrystallization from ethanol/ether afforded the title compound, N-(1-naphthyl)-N'-(3-thiomethylphenyl)-N'-methylguanidine hydrochloride, as a white solid, (760 mg, 52% yield).

mp: 210° C.; $^1$H NMR (300 Mhz, $CD_3OD$) d 7.96–8.01 (m, 3, Ar-H), 7.43–7.66 (m, 6, Ar-H); 7.31–7.34 (m, 2,

Ar-H): 3.59 (s, 3, N-CH$_3$); 2.79 (s, 3, S-CH$_3$); MS (EI): m/e 321 (M$^+$ for free base); Anal. (C$_{19}$H$_{19}$N$_3$S.HCl) Calcd. (%): c 63.76, H 5.63, N 11.74; Found (%): C 63.56, H 5.83, N 11.86.

EXAMPLES 2–6

By procedures similar to those employed in Example 1 above but using appropriately substituted amine hydrochloride and cyanamide reagents, the specified compounds were prepared having the specified physical characteristics.

Example 2—N-(1-Naphthyl)-N'-(3-thiomethylphenyl) guanidine hydrochloride (Formula Ia: hydrochloride salt of R=1-naphthyl, R$^1$=R$^2$=H, R$^4$=m—SCH$_3$)

white solid; mp: 130° C.; $^1$H NMR (300 Mhz, CD$_3$OD) d 8.06–8.11 (d, 1, Ar-H), 7.93–7.94 (d, 1, Ar-H); 7.80–7.87 (m, 2, Ar-H); 7.47–7.61 (m, 7, Ar-H); 2.79 (s, 3, S-CH$_3$); MS (EI): m/e 307 (M$^+$ for free base).

Example 3—N-(1-Naphthyl)-N'-(3-trifluoromethoxyphenyl)-N'-methylguanidine hydrochloride (Formula Ia: hydrochloride salt of R=1-naphthyl, R$^1$=R$^2$=H, R$^4$=m—SCH3)

white solid; mp: 210° C.; $^1$H NMR (300 Mhz, CD$_3$OD) d 7.96–8.02 (m, 3, Ar-H), 7.54–7.65 (m, 7, Ar-H); 7.36–7.39 (d, 1, Ar-H); MS (EI); m/e 359 (M$^+$ for free base); Anal. (C$_{19}$H$_{16}$F$_3$N$_3$O.HCl) Calcd. (%): C 57.66, H 4.33, N 10.62; Found (%): C 57.62, H 4.43, N 10.67.

Example 4—N-(3-Ethylphenyl)-N-methyl-N'-(3-methylthiophenyl)guanidine hydrochloride (Formula Ia: hydrochloride salt of R=3-ethylphenyl, R$^1$=CH$_3$, R$^2$=H, R$^4$=3—SCH$_3$)

mp: 64–65° C.; $^1$ H NMR (CD$_3$OD): ppm 7.50–7.10 (m, ArH, 8H), 3.46 (s, CH$_3$, 3H), 2.74 (q, CH$_2$, 3H), 2.48 (s, CH$_3$, 3H), 1.25 (t, CH$_3$, 3H); MS (EI): m/e 299 (M$^+$: C$_{17}$H$_2$,N$_3$S$_1$); Anal. (C$_{17}$H$_{21}$N$_3$S.HCl); Calcd. (%): C 60.79, H 6.60, N 12.51; Found (%): C 60.43, H 6.61, N 12.20; TLC: R$_f$=0.5 (SiO$_2$, CH$_2$Cl$_2$/MeOH=10/1).

Example 5—N-(3-Methylthiophenyl)-N-methyl-N'-(3-methylthiophenyl)guanidine.HCl (Formula Ia: hydrochloride salt of R=3-methylthiophenyl; R$^1$=CH$_3$, R$^2$=H, R$^4$=3—SCH$_3$)

mp: 75–76° C.; $^1$H NMR (CD$_3$OD): δ ppm 7.50–7.00 (m, ArH, 8H), 3.48 (s, CH$_3$, 3H), 2.52 (s, SCH$_3$, 3H), 2.49 (s, SCH$_3$, 3H); MS (EI): m/e 317.1 (M$^+$: C$_{16}$H$_{19}$N$_3$S$_2$); Anal. (C, H, N; C$_{16}$H$_{19}$N$_3$S$_2$.HCl); Calcd. (%): C 54.30, H 5.70, N 11.87; Found (%): C 54.19, H 5.50, N 11.67; TLC: R$_f$=0.45 (SiO$_2$, CH$_2$Cl$_2$/MeOH=10/1).

Example 6—N-(3-Methylthiophenyl)-N-methyl-N'-(3-bromophenyl)guanidine.HCl (Formula Ia: hydrochloride salt of R=3-methylthiophenyl, R$^1$=CH$_3$, R$_2$=H, R$^4$=3-Br)

mp: 109–110° C.; $^1$H NMR (CD$_3$OD): δ ppm 7.55–7.15 (m, ArH, 8H), 3.48 (s, CH$_3$, 3H), 2.52 (s, SCH$_3$, 3H); MS (EI): m/e 350 (M$^+$: C$_{15}$H$_{16}$N$_3$BrS); Anal. (C, H, N; C$_{15}$H$_{16}$N$_3$BrS.HCl); Calcd. (%): C 46.59, H 4.43, N 10.87; Found (%): C 46.37, H 4.36, N 10.67; TLC: R$_f$=0.47 (SiO$_2$, CH$_2$Cl$_2$/MeOH=10/1).

EXAMPLE 7

PCP Radioligand Binding Assays

PCP receptor binding assays were performed using rat brain membranes as the source of receptors. The radioligand used to label PCP receptors was [$^3$H]MK-801.

Synthesis of [$^3$H]MK-801 and PCP receptor binding assay protocols are described in J. F. W. Keana, et al., *Life Sci.*, 43:965–973 (1988). Briefly, in the protocols, rat brain membranes were prepared and used as described for "detergent-treated membranes" (see D. E. Murphy, et al., *J. Pharmacol. Exp. Ther.*, 240:778–784 (1987)), and stored at a protein concentration of 10 mg/ml at −70° C. No effect of storage (1 month) of the membranes at −70° C. on receptor number or affinity for [$^3$H]MK-801 was observed.

For assays with rat membranes, the thawed membranes were incubated at 1 mg/ml with 0.01% Triton X-100 for 15 minutes at 32° C., then washed three times by centrifugation to reduce the endogenous amino acid concentrations, and finally resuspended in buffer for assay. Glycine and 1-glutamate were each added back to a final concentration of 1 μM to maximally stimulate the [$^3$H]MK-801 binding. The assays contain 400 μl of membranes, and 50 μl of buffer or unlabelled drug.

For [$^3$H]MK-801 binding, 1 nm radioligand was incubated with 200μg/ml of rat brain membranes for 4 hours at room temperature. All assays were stopped by rapid filtration under vacuum through Whatman GF/B glass fiber filters presoaked in 0.05% polyethyleneimine using a Brandel 48-well cell harvester (Brandel, Gaithersburg, Md.). The filters were washed three times with 5 ml of cold 5 mM tris-HCl, pH=7.4. Each filter was suspended in 10 ml of Cytoscint (ICN Biomedicals, Costa Mesa, Calif.) and radioactivity was measured by liquid scintillation spectrometry at a counting efficiency of 50%. Nonspecific binding was defined as that remaining in the presence of 10 μM MK-801 or 100 μM PCP.

Saturation data were evaluated and IC$_{50}$ values were determined as described by J. B. Fischer and A. Schonbrunn (*J. Biol. Chem.*, 263:2808–2816 (1988)), and Ki values were derived from the IC$_{50}$ values as described by Cheng and Pousoff (*Biochem. Phamacol.*, 22:3099–3108 (1973).

Results of the assay are shown in Table I which follows Example 8 below, wherein the general formula of the tested compounds is shown at the top of Table I with the particular substituent groups of each compound specified within the Table.

EXAMPLE 8

Sigma Receptor Binding Assay

Methods. Sigma receptor binding assays using guinea pig brain membrane homogenates and the radioligand [$^3$H]DTG were conducted as described by E. Weber, et al., *P.N.A.S. (USA)*, 83:8784–8788 (1986). Briefly, frozen whole guinea-pig brains (Biotrol, Indianapolis, Ind.) were homogenized in 10 volumes (w/v) of ice-cold 320 mM sucrose using a Brinkman polytron. The homogenate was centrifuged at 1,000×g for 20 minutes at 4° C. The supernatant was centrifuged at 20,000×g for 20 minutes at 4° C. The resulting pellet was resuspended in 10 initial volumes of 50 mM Tris/HCl buffer at pH 7.4 and centrifuged at 20,000×g for 20 minutes at 4° C. The resulting pellet was resuspended in 5 initial volumes ice-cold 50 mM Tris/HCl (pH 7.4), and the final volume was adjusted to yield a protein concentration of 3 mg/ml. Aliquots of 20-ml were stored at −70° C. until used, with no detectable loss of binding.

For [$^3$H]DTG binding assays, the frozen membrane suspensions were thawed and diluted 1:3 in 50 mM Tris/HCl (pH 7.4). To 12×75 mm polystyrene test tubes were added 0.8 ml of diluted membrane suspension, 0.1 ml of [$^3$H]DTG (Dupont/NEN) to yield a final concentration of 1.4 nM, and 0.1 ml of unlabelled drugs or buffer. The protein concentration in the 1-ml final incubation volume was 800 μg/ml, corresponding to 32 mg of brain tissue (original wet weight) and to a tissue concentration within the linear range for specific binding. Non-specific binding was defined as that remaining in the presence of 10 μM haloperidol. Incubations were terminated after 90 minutes at room temperature by additional of 4 ml of ice-cold 50 mM Tris/HCl (pH 7.4) and rapid filtration of the membrane suspension through Whatman GF/B glass-fiber filters under vacuum, using a 48-well cell harvester (Brandel). The filters were washed 2 times with 4 ml of 50 mM Tris/HCl (pH 7.4). Each filter was suspended in 10 ml Cytoscint (ICI), and radioactivity was measured to liquid scintillation spectrometry at a counting efficiency of approximately 50%. $IC_{50}$ values were determined by non-linear regression analysis. The results are shown in Table I below for each of the tested compounds of the specified structure.

TABLE I

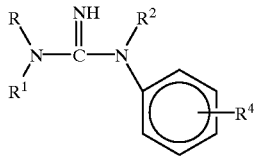

| Compd. No. | R | $R^1$ | $R^2$ | $R^4$ | [³H-MK801] Ki (nM) | [³H-MK801] $IC_{50}$ (nM) | [³H-DTG] $IC_{50}$ (nM) |
|---|---|---|---|---|---|---|---|
| 1 | 1-naphthyl | H | $CH_3$ | 3-$SCH_3$ | 32.8 | 42.6 | 1658 |
| 2 | 1-naphthyl | H | $CH_3$ | 3-$OCF_3$ | 48.8 | 63.4 | 1455 |
| 3 | 1-naphthyl | H | $CH_3$ | 3-$S(O)CH_3$ | 324.6 | 421 | |
| 4 | 1-naphthyl | H | H | 3-$SCH_3$ | 95.4 | 124 | 27 |
| 5 | 1-naphthyl | H | H | 3-$S(O)CH_3$ | 655.4 | 852 | 228 |
| 6 | 1-naphthyl | H | H | 3-$S(O)_2CH_3$ | 630.8 | 820 | 183 |
| 7 | 3-ethylphenyl | $CH_3$ | H | 3-$SCH_3$ | 20.9 | 20 | |
| 8 | 3-($SCH_3$)phenyl | $CH_3$ | H | 3-$SCH_3$ | 6.4 | 5.5 | |
| 9 | 3-bromophenyl | H | $CH_3$ | 3-$SCH_3$ | 34.3 | 30 | |

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method of treating a mammal suffering from a disease of the nervous system in which the pathophysiology of the disorder involves excessive excitation of nerve cells by agonists of NMDA receptors, comprising administering to the mammal an effective amount of a compound that is selected from the group consisting of N-(1-naphthyl)-N'-(3-methylthiophenyl)-N'-methylguanidine;
N-(1-naphthyl)-N-methyl-N'-(3-methylthiophenyl)guanidine;
N-(1-naphthyl)-N,N'-dimethyl-N'-(3-methylthiophenyl)guanidine;
N-(1-naphthyl)-N'-(3-methylthiophenyl)guanidine;
N-(1-naphthyl)-N'-(3-methylsulfinylphenyl)-N'-methylguanidine;
N-(1-naphthyl)-N-methyl-N'-(3-methylsulfinylphenyl)guanidine;
N-(1-naphthyl)-N,N'-dimethyl-N'-(3-methylsulfinylphenyl)guanidine;
N-(1-naphthyl)-N'-(3-methylsulfinylphenyl)guanidine;
N-(1-naphthyl)-N'-(3-methylsulfonylphenyl)-N'-methylguanidine;
N-(1-naphthyl)-N-methyl-N'-(3-methylsulfonylphenyl)guanidine;
N-(1-naphthyl)-N,N'-dimethyl-N'-(3-methylsulfonylphenyl)guanidine;
N-(1-naphthyl)-N'-(3-methylsulfonylphenyl)guanidine;
N-(1-naphthyl)-N'-(3-trifluoromethylthiophenyl)-N'-methylguanidine;
N-(1-naphthyl)-N-methyl-N'-(3-tifluoromethylthiophenyl)guanidine;
N-(1-naphthyl)-N,N'-dimethyl-N'-(3-trifluoromethylthiophenyl)guanidine;
N-(1-naphthyl)-N'-(3-trifluoromethylthiophenyl)guanidine;
N-(1-naphthyl)-N'-(3-trifluoromethoxyphenyl)-N'-methylguanidine;
N-(1-naphthyl)-N-methyl-N'-(3-trifluoromethoxyphenyl)-N'-methylguanidine;
N-(1-naphthyl)-N'-(3-trifluoromethoxyphenyl)guanidine;
N-(3-ethylphenyl)-N'-(3-methylthiophenyl)-N'-methylguanidine;
N-(3-ethylphenyl)-N,N'-dimethyl-N'-(3-methylthiophenyl)guanidine;
N-(3-ethylphenyl)-N'-(3-methylthiophenyl)guanidine;
N-(3-ethylphenyl)-N'-(3-methylsulfinylphenyl)-N'-methylguanidine;
N-(3-ethylphenyl)-N,N'-dimethyl-N'-(3-methylsulfinylphenyl)guanidine;
N-(3-ethylphenyl)-N'-(3-methylsulfinylphenyl)guanidine;
N-(3-ethylphenyl)-N'-(3-methylsulfinylphenyl)-N'-methylguanidine;
N-(3-ethylphenyl)-N,N'-dimethyl-N'-(3-methylsulfonylphenyl)guanidine;
N-(3-ethylphenyl)-N'-(3-methylsulfonylphenyl)guanidine;
N-(3-ethylphenyl)-N'-(3-trifluoromethylthiophenyl)-N'-methylguanidine;
N-(3-ethylphenyl)-N-methyl-N'-(3-trifluoromethylthiophenyl)guanidine;
N-(3-ethylphenyl)-N,N'-dimethyl-N'-(3-trifluoromethylthiophenyl)guanidine;

N-(3-ethylphenyl)-N'-(3-trifluoromethylthiophenyl) guanidine;

N-(3-ethylphenyl)-N-methyl-N'-(3-trifluoromethyphenyl)guanidine;

N-(3-ethylphenyl)-N-methyl-N'-(3-trifluoromethoxyphenyl)-N'-methylguanidine;

N-(3-ethylphenyl)-N-methyl-N'-(3-trifluoromethoxyphenyl)guanidine; and

N-(3-ethylphenyl)-N'-(3-trifluoromethoxyphenyl) guanidine; or a pharmaceutically acceptable salt thereof.

2. A method of treating a mammal suffering from a disease of the nervous system in which the pathophysiology of the disorder involves excessive excitation of nerve cells by agonists of NMDA receptors, comprising administering to the mammal an effective amount of a compound that is selected from the group consisting of N-(3-methylthiophenyl)-N'-(3-methylthiophenyl) guanidine;

N-(3-methylthiophenyl)-N'-(3-methylthiophenyl)-N'-methylguanidine;

N-(3-methylthiophenyl)-N,N'-dimethyl-N'-(3-methylthiophenyl)guanidine;

N-(3-methylthiophenyl)-N'-(3-bromophenyl)guanidine;

N-(3-methylthiophenyl)-N'-(3-bromophenyl)-N'-methylguanidine;

N-(3-methylthiophenyl)-N-methyl-N'-(3-bromophenyl) guanidine; and

N-(3-methylthiophenyl)-N,N'-dimethyl-N'-(3-bromophenyl)guanidine; or a pharmaceutically acceptable salt thereof.

3. A method of claim 2 wherein the administered compound is N-(3-methylthiophenyl)-N'-(3-methylthiophenyl)-N'-methylguanidine, or a pharmaceutically acceptable thereof.

4. A method of treating a mammal suffering from or susceptible to Alzheimer's disease, Parkinson's disease, Huntington's disease, Amyotrophic Lateral Sclerosis, Down's Syndrome, Korsakff's Disease or epilepsy, comprising administering to the mammal an effective amount of a compound selected from the group consisting of:

N-(1-naphthyl)-N'-(3-methythiophenyl)-N'-methylguanidine;

N-(1-naphthyl)-N-methyl-N'-(3-methylthiophenyl) guanidine;

N-(1-naphthyl)-N,N'-dimethyl-N'-(3-methylthiophenyl) guanidine;

N-(1-naphthyl)-N'-(3-methylthiophenyl)guanidine;

N-(1-naphthyl)-N'-(3-methylsulfinylphenyl)-N'-methylguanidine;

N-(1-naphthyl)-N-methyl-N'-(3-methylsufinylphenyl) guanidine;

N-(1-naphthyl)-N,N'-dimethyl-N'-(3-methylsufinylphenyl)guanidine;

N-(1-naphthyl)-N'-(3-methylsulfinylphenyl)guanidine

N-(1-naphthyl)-N'-(3-methylsulfonylphenyl)-N'-methylguanidine;

N-(1-naphthyl)-N-methyl-N'-(3-methylsulfonylphenyl guanidine;

N-(1-naphthyl)-N,N'-dimethyl-N'-(3-methylsulfonylphenyl)guanidine;

N-(1-naphthyl)-N'-(3-methylsulfonylphenyl)guanidine;

N-(1-naphthyl)-N'-(3-trifluoromethylthiophenyl)-N'-methylguanidine;

N-(1-naphthyl)-N-methyl-N'-(3-trifluoromethylthiophenyl)guanidine;

N-(1-naphthyl)-N,N'-dimethyl-N'-(3-trifluoromethylthiophenyl)guanidine;

N-(1-naphthyl)-N'-(3-trifluoromethylthiophenyl) guanidine;

N-(1-naphthyl)-N'-(3-trifluoromethoxyphenyl)-N'-methylguanidine;

N-(1-naphthyl)-N-methyl-N'-(3-trifluoromethoxyphenyl)-N'-methylguanidine;

N-(1-naphthyl)-N'-(3-trifluoromethoxyphenyl)guanidine;

N-(3-ethylphenyl)-N'-(3-methylthiophenyl)-N'-methylguanidine;

N-(3-ethylphenyl)-N,N'-dimethyl-N'-(3-methylthiophenyl)guanidine;

N-(3-ethylphenyl)-N'-(3-methylthiophenyl)guanidine;

N-(3-ethylphenyl)-N'-(3-methylsulfinylphenyl)-N'-methylguanidine;

N-(3-ethylphenyl)-N,N'-dimethyl-N'-(3-methylsulfinylphenyl)guanidine;

N-(3-ethylphenyl)-N'-(3-methylsulfinylphenyl) guanidine;

N-(3-ethylphenyl)-N'-(3-methylsulfonylphenyl)-N'-methylguanidine;

N-(3-ethylphenyl)-N,N'-dimethyl-N'-(3-methylsulfonylphenyl)guanidine;

N-(3-ethylphenyl)-N'-(3-methylsulfonylphenyl) guanidine;

N-(3-ethylphenyl)-N'-(3-trifluoromethylthiophenyl)-N'-methylguanidine;

N-(3-ethylphenyl)-N-methyl-N'-(3-trifluoromethylthiophenyl)guanidine;

N-(3-ethylphenyl)-N,N'-dimethyl-N'-(3-trifluoromethylthiophenyl) guanidine;

N-(3-ethylphenyl)-N'-(3-trifluoromethylthiophenyl) guanidine;

N-(3-ethylphenyl)-N-methyl-N'-(3-trifluoromethoxyphenyl)guanidine;

N-(3-ethylphenyl)-N-methyl-N'-(3-trifluoromethoxyphenyl)-N'-methylguanidine;

N-(3-ethylphenyl)-N-methyl-N'-(3-trifluoromethoxyphenyl)guanidine; and

N-(3-ethylphenyl)-N'-(3-trifluoromethoxyphenyl) guanidine; or a pharmaceutically acceptable salts thereof.

5. A method of treating a mammal suffering from or susceptible to Alzheimer's disease, Parkinson's disease, Huntington's disease, Amyotrophic Lateral Sclerosis, Down's Syndrome, Korsakoff's Disease or epilepsy, comprising administering to the mammal an effective amount of a compound selected from the group consisting of:

N-(3-methylthiophenyl)-N'-(3-methylthiophenyl) guanidine;

N-(3-methylthiophenyl)-N'-(3-methylthiophenyl)-N'-methylguanidine;

N-(3-methylthiophenyl)-N,N'-dimethyl-N'-(3-methylthiophenyl)guanidine;

N-(3-methylthiophenyl)-N'-(3-bromophenyl)guanidine;

N-(3-methylthiophenyl) -N'-(3-bromophenyl)-N'-methylguanidine;

N-(3-methylthiophenyl)-N-methyl-N'-(3-bromophenyl) guanidine; and

N-(3-methylthiophenyl)-N,N'-dimethyl-N'-(3-bromophenyl)guanidine; or a pharmaceutically acceptable salt thereof.

6. A method of claim 5 wherein the administered compound is N-(3-methylthiophenyl)-N'-(3-methylthiophenyl)-N'-methylguanidine, or a pharmaceutically acceptable thereof.

7. A method of treating a mammal suffering from or susceptible to a neurodegenerative disease, comprising administering to the mammal an effective amount of a compound of selected from the group consisting of:

N-(1-naphthyl)-N'-(3-methylthiophenyl)-N'-methylguanidine;
N-(1-naphthyl)-N-methyl-N'-(3-methylthiophenyl) guanidine;
N-(1-naphthyl)-N,N'-dimethyl-N'-(3-methylthiophenyl)guanidine;
N-(1-naphthyl)-N'-(3-methylthiophenyl)guanidine;
N-(1-naphthyl)-N'-(3-methylsulfinylphenyl)-N'-methylguanidine;
N-(1-naphthyl)-N-methyl-N'-(3-methylsulfinylphenyl) guanidine;
N-(1-naphthyl)-N,N'-dimethyl-N'-(3-methylsulfinylphenyl)guanidine;
N-(1-naphthyl)-N'-(3-methylsulfinylphenyl)guanidine;
N-(1-naphthyl)-N'-(3-methylsulfinylphenyl)-N'-methylguanidine;
N-(1-naphthyl)-N-methyl-N'-(3-methylsulfonylphenyl) guanidine;
N-(1-naphthyl)-N,N'-dimethyl-N'-(3-methylsulfonylphenyl)guanidine;
N-(1-naphthyl)-N'-(3-methylsulfonylphenyl)guanidine;
N-(1-naphthyl)-N'-(3-trifluoromethylthiophenyl)-N'-methylguanidine;
N-(1-naphthyl)-N-methyl-N'-(3-trifluoromethylthiophenyl)guanidine;
N-(1-naphthyl)-N,N'-dimethyl-N'-(3-trifluoromethylthiophenyl)guanidine;
N-(1-naphthyl)-N'-(3-trifluoromethylthiophenyl) guanidine;
N-(1-naphthyl)-N'-(3-trifluoromethoxyphenyl)-N'-methylguanidine;
N-(1-naphthyl)-N-methyl-N'-(3-trifluoromethoxyphenyl)-N'-methylguanidine;
N-(1-naphthyl)-N'-(3-trifluoromethoxyphenyl)guanidine;
N-(3-ethylphenyl)-N'-(3-methylthiophenyl)-N'-methylguanidine;
N-(3-ethylphenyl)-N,N'-dimethyl-N'-(3-methylthiophenyl)guanidine;
N-(3-ethylphenyl)-N'-(3-methylthiophenyl)guanidine;
N-(3-ethylphenyl)-N'-(3-methylsulfinylphenyl)-N'-methylguanidine;
N-(3-ethylphenyl)-N,N'-dimethyl-N'-(3-methylsulfinylphenyl)guanidine,
N-(3-ethylphenyl)-N'-(3-methylsulfinylphenyl) guanidine;
N-(3-ethylphenyl)-N'-(3-methylsulfonylphenyl)-N'-methylguanidine;
N-(3-ethylphenyl)-N,N'-dimethyl-N'-(3-methylsulfonylphenyl)guanidine;
N-(3-ethylphenyl)-N'-(3-methylsulfonylphenyl) guanidine;
N-(3-ethylphenyl)-N'-(3-trifluoromethylthiophenyl)-N'-methylguanidine;
N-(3-ethylphenyl)-N-methyl-N'-(3-trifluoromethylthiophenyl)guanidine;
N-(3-ethylphenyl)-N,N'-dimethyl-N'-(3-trifluoromethylthiophenyl) guanidine;
N-(3-ethylphenyl)-N'-(3-trifluoromethylthiophenyl) guanidine;
N-(3-ethylphenyl)-N-methyl-N'-(3-trifluoromethoxyphenyl)guanidine;
N-(3-ethylphenyl)-N-methyl-N'-(3-trifluorormethoxyphenyl)-N'-methylguanidine;
N-(3-ethylphenyl)-N-methyl-N'-(3-trifluoromethoxyphenyl)guanidine; and
N-(3-ethylphenyl)-N'-(3-trifluoromethoxyphenyl) guanidine; or a pharmaceutically acceptable salts thereof.

8. A method of treating a mammal suffering from or susceptible to a neurodegenerative disease, comprising administering to the mammal an effective amount of a compound of selected from the group consisting of:

N-(3-methylthiophenyl)-N'-(3-methylthiophenyl) guanidine;
N-(3-methylthiophenyl)-N'-(3-methylthiophenyl)-N'-methylguanidine;
N-(3-methylthiophenyl)-N,N'-dimethyl-N'-(3-methylthiophenyl)guanidine;
N-(3-methylthiophenyl)-N'-(3-bromophenyl)guanidine;
N-(3-methylthiophenyl)-N'-(3-bromophenyl)-N'-methylguanidine;
N-(3-methylthiophenyl)-N-methyl-N'-(3-bromophenyl) guanidine; and
N-(3-methylthiophenyl)-N,N'-dimethyl-N'-(3-bromophenyl)guanidine; and
pharmaceutically acceptable salts thereof.

9. A method of claim 8 wherein the administered compound is N-(3-methylthiophenyl)-N'-(3-methylthiophenyl)-N'-methylguanidine, or a pharmaceutically acceptable thereof.

* * * * *